United States Patent
Cohen et al.

(10) Patent No.: US 11,129,574 B2
(45) Date of Patent: Sep. 28, 2021

(54) REAL TIME ELECTROANATOMICAL COLORING OF THE HEART

(71) Applicant: BIOSENSE WEBSTER (ISRAEL) LTD., Yokneam (IL)

(72) Inventors: Assaf Cohen, Kiryat Bialik (IL); Lilia Suzdalnitsky, Haifa (IL); Eduard Filipov, Karmiel (IL); Ido Ilan, Yoqneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 67 days.

(21) Appl. No.: 15/375,358

(22) Filed: Dec. 12, 2016

(65) Prior Publication Data

US 2018/0160978 A1 Jun. 14, 2018

(51) Int. Cl.
*A61B 5/287* (2021.01)
*A61B 5/00* (2006.01)
(Continued)

(52) U.S. Cl.
CPC .............. *A61B 5/6858* (2013.01); *A61B 5/01* (2013.01); *A61B 5/065* (2013.01); *A61B 5/287* (2021.01); *A61B 5/6859* (2013.01); *A61B 5/742* (2013.01); *A61B 5/743* (2013.01); *A61B 5/7425* (2013.01); *A61B 18/1492* (2013.01); *G06T 7/0012* (2013.01); *A61B 5/316* (2021.01); *A61B 5/4848* (2013.01); *A61B 5/7285* (2013.01); *A61B 2018/00267* (2013.01); *A61B 2018/00577* (2013.01); *A61B 2018/00702* (2013.01); *A61B 2018/00791* (2013.01); *A61B 2018/00839* (2013.01); *A61B 2018/00875* (2013.01); *A61B 2018/1435* (2013.01); *A61B 2505/05* (2013.01); *A61B 2562/0257* (2013.01);
(Continued)

(58) Field of Classification Search
None
See application file for complete search history.

(56) References Cited

U.S. PATENT DOCUMENTS 5,687,737 A  11/1997  Branham et al.
5,738,096 A   4/1998  Ben-Haim
(Continued)

FOREIGN PATENT DOCUMENTS

EP    2550914    1/2013
EP    2848191    3/2015
(Continued)

OTHER PUBLICATIONS

European Search Report and Written Opinion for Europe Patent Application No. 17206483.4; dated Apr. 24, 2018.
(Continued)

*Primary Examiner* — Ankit D Tejani

(57) ABSTRACT

Cardiac catheterization is conducted with a probe having a plurality of sensors. The heart is displayed as a first graphic image. Signals from the sensors are processed according to a predefined algorithm to generate respective outputs, A region on the first graphic image that is less than all of the first graphic image is selected according to locations of the sensors, and values derived from outputs of the sensors are displayed on the selected region as a second graphic image. Thereafter, the second graphic image is removed and replaced by an updated version.

14 Claims, 3 Drawing Sheets

(51) Int. Cl.
  *A61B 5/01* (2006.01)
  *A61B 5/06* (2006.01)
  *A61B 18/14* (2006.01)
  *G06T 7/00* (2017.01)
  *A61B 18/00* (2006.01)
  *A61B 5/316* (2021.01)

(52) U.S. Cl.
  CPC . *A61B 2562/0271* (2013.01); *A61B 2576/023* (2013.01); *G06T 2207/30048* (2013.01)

(56) References Cited

U.S. PATENT DOCUMENTS

| | | | |
|---|---|---|---|
| 6,226,542 | B1 | 5/2001 | Reisfeld |
| 6,301,496 | B1 | 10/2001 | Reisfeld |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,517,318 | B2 | 4/2009 | Altmann et al. |
| 7,536,218 | B2 | 5/2009 | Govari et al. |
| 7,756,576 | B2 | 7/2010 | Levin |
| 8,428,700 | B2 | 4/2013 | Harlev et al. |
| 8,478,383 | B2 | 7/2013 | Bar-Tal et al. |
| 9,265,434 | B2 | 2/2016 | Merschon et al. |
| 9,271,680 | B2 | 3/2016 | Dubois et al. |
| 9,615,764 | B2 | 4/2017 | Zino et al. |
| 9,662,033 | B2 | 5/2017 | Severino |
| 9,713,435 | B2 | 7/2017 | Govari et al. |
| 2006/0116576 | A1 | 6/2006 | McGee et al. |
| 2007/0049817 | A1 | 3/2007 | Preiss et al. |
| 2008/0137927 | A1 | 6/2008 | Altmann et al. |
| 2008/0300487 | A1 | 12/2008 | Govari et al. |
| 2009/0099468 | A1 | 4/2009 | Thiagalingam et al. |
| 2009/0148012 | A1 | 6/2009 | Altmann et al. |
| 2009/0177089 | A1 | 7/2009 | Govari et al. |
| 2011/0144510 | A1 | 6/2011 | Ryu et al. |
| 2011/0144524 | A1 | 6/2011 | Fish et al. |
| 2012/0184863 | A1 | 7/2012 | Harlev et al. |
| 2013/0041235 | A1 | 2/2013 | Rogers et al. |
| 2013/0109945 | A1 | 5/2013 | Harlev et al. |
| 2013/0131496 | A1* | 5/2013 | Jenkins ............... A61B 5/055 600/411 |
| 2014/0081262 | A1 | 3/2014 | Koblish et al. |
| 2015/0305812 | A1 | 10/2015 | Govari et al. |
| 2016/0026367 | A1* | 1/2016 | Brown ............ H04M 1/72552 715/835 |
| 2016/0073913 | A1 | 3/2016 | Francis et al. |
| 2016/0095530 | A1* | 4/2016 | Dubois ............. A61B 5/0044 600/512 |
| 2016/0120427 | A1 | 5/2016 | Zino et al. |
| 2016/0183824 | A1 | 6/2016 | Severino |
| 2017/0109016 | A1* | 4/2017 | Hachiya ............ G06F 3/04883 |

FOREIGN PATENT DOCUMENTS

| | | |
|---|---|---|
| EP | 3015060 | 5/2016 |
| JP | 2013-027705 A | 2/2013 |
| JP | 2013-537096 A | 9/2013 |
| JP | 2016-019753 A | 2/2016 |
| JP | 2016-087464 A | 5/2016 |
| JP | 2016-123870 A | 7/2016 |
| WO | 06/060613 | 6/2006 |
| WO | 14/174274 | 10/2014 |

OTHER PUBLICATIONS

Search Report from corresponding Japanese Patent Application No. 2017-236659 dated Jul. 28, 2021.
Notice of Reasons for Refusal from corresponding Japanese Patent Application No. 2017-236659 dated Aug. 3, 2021.

* cited by examiner

REAL TIME ELECTROANATOMICAL COLORING OF THE HEART

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to measurement of bioelectric currents. More particularly, this invention relates to systems for recording bioelectric signals from the heart using means inserted into the body.

2. Description of the Related Art

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include reentrant areas, which may be associated with signal patterns known as complex fractionated electrograms. Once a defect is located by such mapping, it may be ablated (if it is functioning abnormally) or otherwise treated to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode was, furthermore, a lengthy procedure, generally performed under fluoroscopic imaging, and thereby exposing the patient to undesirable ionizing radiation. Furthermore, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described. Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

Commonly assigned U.S. Patent Application Publication No. 20160120427 by Zino et al., whose disclosure is herein incorporated by reference, describes near realtime data display of electroanatomic data obtained from the heart on a monitor. During a time interval that does not exceed a duration of a cardiac cycle of the heart the following steps are performed: reading data from at least one of the electrodes and sensors, and invoking a processor to perform an algorithm on the data. The data is one of a plurality of inputs of the algorithm, and the result of the algorithm includes a transformation of the data. The result of the algorithm is rendered on the monitor to modify an electroanatomical map.

SUMMARY OF THE INVENTION

In a conventional cardiac catheterization procedure a colored electroanatomic map is stable until the user starts to ablate. Once the user has begun ablation, the electroanatomical behavior of the heart changes, but the displayed map remains the same. To see the results of the ablation, the user needs to create a new map and recolor it. This takes time and effort.

According to disclosed embodiments of the invention, in one mode of operation a map that is initially monocolored, e.g., gray, is presented and colored. Periodically the coloring is removed, and the map recolored based on updated information. The user selects regions of the map using any catheters being used. These regions are colored in real time according to the value of a parameter to present a functional display. The parameter represented by the coloring can be selected by the user, e.g., unipolar potentials, bipolar potentials, or local activation times.

There is provided according to embodiments of the invention a method of catheterization, which is carried out by inserting a probe into a heart of a living subject, the distal portion of the probe having a plurality of sensors disposed thereon. The method is further carried out iteratively by displaying the heart as a first graphic image, processing signals from the sensors according to a predefined algorithm to generate respective outputs, selecting a region on the first graphic image that is less than all of the first graphic image, graphically displaying at least a portion of the outputs on the selected region as a second graphic image, and thereafter removing the second graphic image.

According to one aspect of the method, the sensors are electrodes and the signals are bioelectric voltages.

According to a further aspect of the method, the predefined algorithm includes a calculation of wavefront propagation and the outputs are local activation times at respective locations of the sensors.

According to yet another aspect of the method, the sensors are temperature sensors.

According to still another aspect of the method, the sensors are contact force sensors.

According to another aspect of the method, the sensors are location sensors.

According to an additional aspect of the method, removing the second graphic image is performed after elapse of a time interval.

One aspect of the method includes gating signals from the sensors according to a cardiorespiratory cycle.

There is further provided according to embodiments of the invention an apparatus, including a probe having a plurality of electrodes and sensors, electrical circuitry for receiving data from the electrodes and sensors when the probe is at a location in a heart of a living subject, a memory, a display monitor, and a processor connected to the memory and the display monitor. The apparatus is operative for iteratively displaying the heart as a first graphic image, processing signals from the sensors according to a predefined algorithm to generate respective outputs, selecting a region on the first graphic image that is less than all of the first graphic image, graphically displaying at least a portion of the outputs on the selected region as a second graphic image, and thereafter removing the second graphic image.

The apparatus may include gating circuitry linked to signals from the sensors, the gating circuitry operative for gating the sensor outputs according to the cardiorespiratory cycle.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
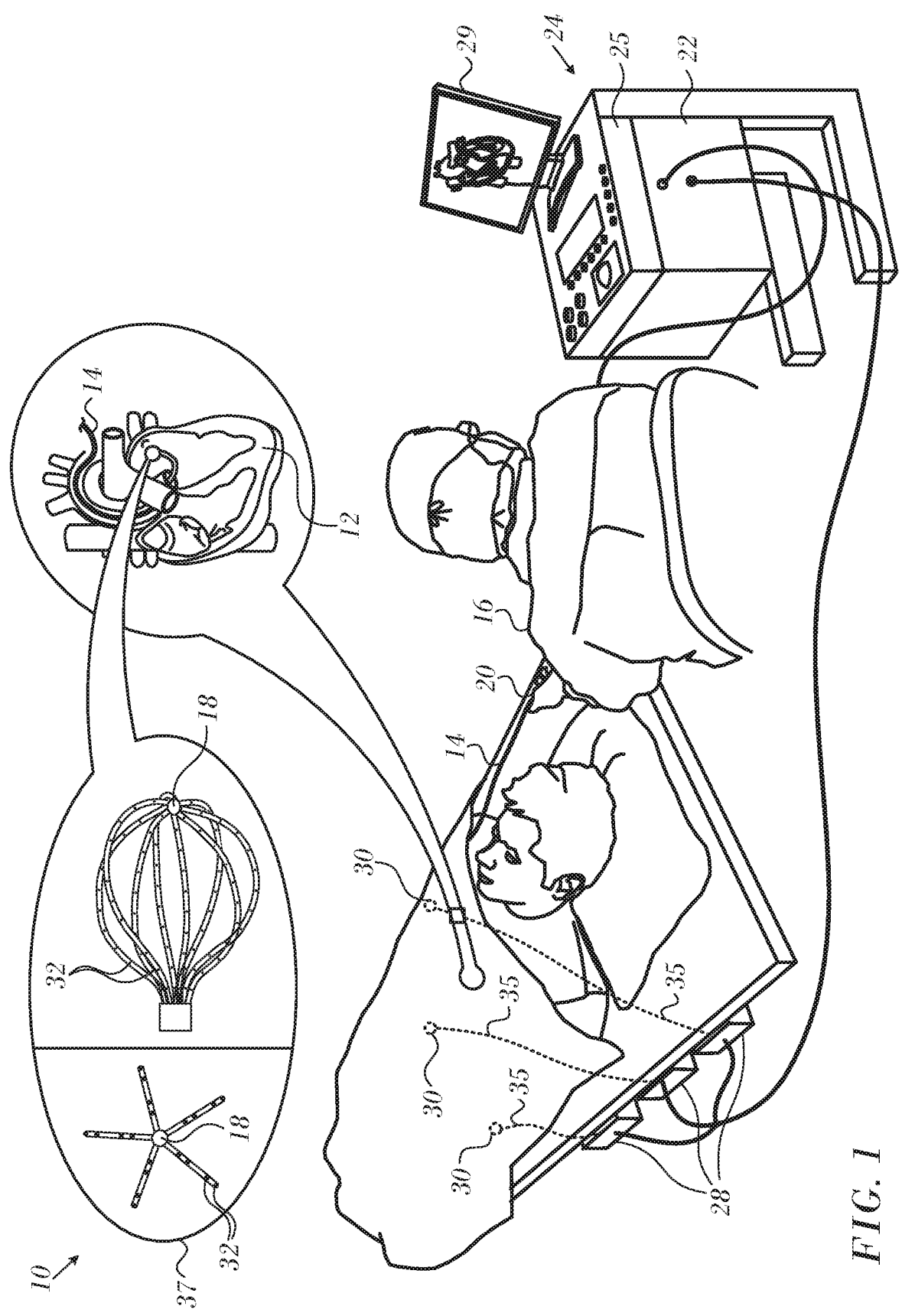
FIG. 1 is a pictorial illustration of a system for evaluating electrical activity in a heart, which is constructed and operative in accordance with a disclosed embodiment of the invention.

Turning now to the drawings, reference is initially made to FIG. 1, which is a pictorial illustration of a system 10 for evaluating electrical activity in a heart of a living subject, which is constructed and operative in accordance with a disclosed embodiment of the invention. The system comprises a catheter 14, which is percutaneously inserted by an operator 16 through the patient's vascular system into a chamber or vascular structure of a heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from 30 Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A sensor for obtaining a physiological parameter, such as an electrode or temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits, which may include gating circuitry that can be configured for gating sensor readings according to the cardiorespiratory cycle. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images that are described below.

Operation.

Figure 2:
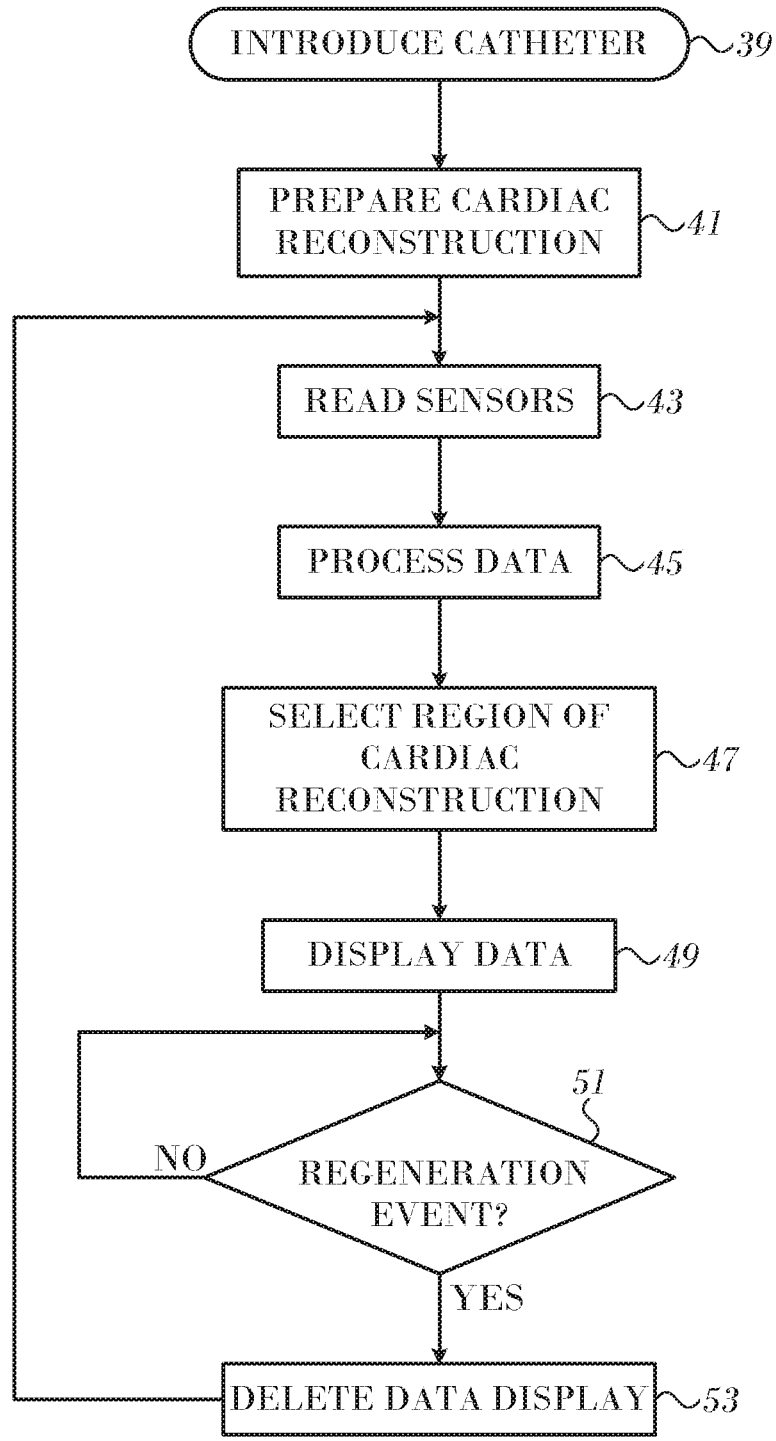
FIG. 2 is a flow chart of a method for real-time coloring of an electrophysiological map of the heart in accordance with an embodiment of the invention.

Reference is now made to FIG. 2, which is a flow chart of a method for real-time coloring of an electrophysiological map of the heart in accordance with an embodiment of the invention. The process steps are shown in a particular linear sequence in FIG. 2 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the process.

At initial step 39 one or more cardiac catheters are introduced into the heart of a subject using well-known methods.

Next, at step 41 a reconstruction of the structure of the heart or the chamber is prepared, i.e., geometrically defined in 3-dimensional space. This can be accomplished by analysis of images from other modalities, i.e., segmentation from pre-acquired magnetic resonance images or fluoroscopy images that have been registered with model of the chamber. Registration of images acquired or prepared by different modalities is known, for example from U.S. Patent Application Publication No. 2007/0049817, and commonly assigned U.S. Pat. No. 7,517,318 to Altmann et al., which are herein incorporated by reference. Yet another method of generating the reconstruction is disclosed in commonly assigned U.S. Pat. No. 9,265,434 to Merschon et al., entitled Dynamic Feature Rich Anatomical Reconstruction from a Point Cloud, which is herein incorporated by reference. In this method, the atrium shape is represented as the isosurface of a field function, defined at all points within a bounding domain Other methods of reconstruction are known in the art and may be used, for example the methods disclosed in U.S. Pat. No. 6,226,542 to Reisfeld, and U.S. Patent Application Publication No. 2009/0177089 by Govari et al., which are commonly assigned herewith and incorporated by reference. Alternatively, the CARTOMERGE™ module and other facilities of the above-noted CARTO system can accomplish this step using images of the heart prepared at the same or a different session.

At the completion of step 41 the reconstruction is displayed in a single color or shade, without contrast. At this stage the representation conveys no functional electroanatomic information, but simply depicts a model of the structure of the subject's heart.

Next at step 43 one or more sensors on the catheter are read out. The sensors may be a selected group of electrodes on a multielectrode catheter, for example electrodes on a spline, or a set of electrodes known to be in contact with the endocardium. The sensors can be, for example, location sensors that are components of the above-described positioning system (FIG. 1), mapping electrodes, or sensors of physical states such as temperature, voltages and electrical phase information, contact force, or a combination thereof.

While it is possible to graphically display the raw data on the monitor 29 (FIG. 1), e.g., temperature readings from thermocouples on the catheter. More commonly, at step 45 data is accumulated over a time interval and processed according to some algorithm in order to develop a functional electroanatomic map. For example, voltages may be accumulated over a cardiac cycle to derive spatial LAT's. As another example, the second derivative of reflectance data may be displayed, as described in commonly assigned U.S. Patent Application Publication No. 20150305812 by Govari et al., entitled Prevention of Steam Pops during Ablation, which is herein incorporated by reference. In all such cases, the values of the information measured or derived may be conveniently shown on the monitor 29 in pseudocolors representing ranges of values. In the case of electrodes, the information may be gated to the cardiorespiratory cycle and could be unipolar or bipolar potentials.

Next, at step 47 a region of 3-dimensional space of the cardiac reconstruction prepared in step 41 is selected for display. The region is automatically created based on current locations of sensors on the catheter, and the display spatially indicates information derived from readings of the sensors. The radius influenced at the locations, and thus the size of the displayed region is user-definable.

The information in the regional display may be represented in the as pseudocolors as known in the art, or may be shown in any other suitable graphic display Nonselected areas remain in monocolor. As creating and updating the display is limited to an area of interest, the algorithm may execute more rapidly, sparing computer resources, as it is not necessary to redraw a functional map of the entire heart. Moreover, the operator is protected from information overload.

Next, at step 49 after reading data from the sensors and processing the data as required in step 45, the output values are displayed in pseudocolor only on the region chosen in step 47. Processing the data can be, for example, a calculation of wavefront propagation and the output values can be local activation times at respective locations of the sensors.

Once the information is displayed, control proceeds to a delay step 51, where an event leading to regeneration of the display of step 49 is awaited. The event may be elapse of a predefined time interval.

Next, at step 53 the display of step 49 is erased, transiently resulting in the reappearance of a monocolored image on the monitor 29, depending on the system performance. Control then returns to step 43 to iterate the display process, using new readings of the sensors. A different region may be selected in step 47, particularly if the catheter has been navigated in the heart since the previous iteration. In one embodiment, the regional display is deleted and updated with new data every 16 ms, or once during each gating interval, according to the current mode of operation.

Example

Figure 3:
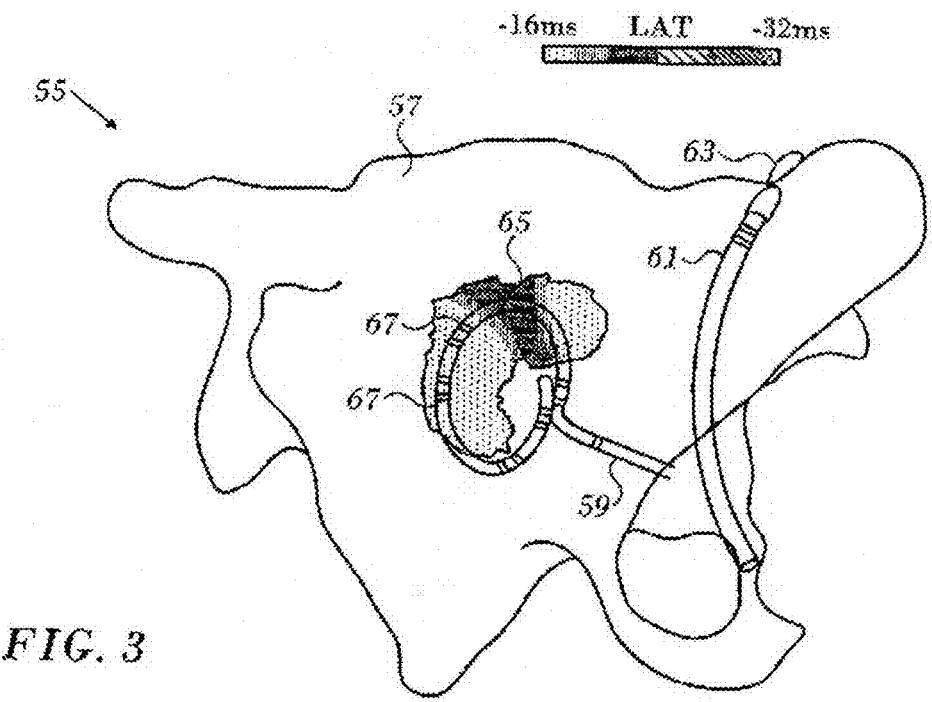
FIG. 3 is a screen display that was produced during a cardiac catheterization in accordance with an embodiment of the invention.

Reference is now made to FIG. 3, which is a screen display 55 that was produced during a cardiac catheterization in accordance with an embodiment of the invention. A reconstruction 57 of the left atrium of the heart is shown as a mostly monocolored grey form. Catheters 59, 61 have been inserted into the heart. Catheter 61 is an ablation catheter whose distal end lies in a pulmonary vein ostium. Colored area 63 near the tip of the catheter represents temperature at an ablation site in the ostium. Catheter 59 is a lasso catheter having multiple mapping electrodes 67. A colored area 65 about some of the electrodes 67 is a map of local activation time in the region, which may vary as the ablation proceeds. Colored areas 63, 65 are represented by different hatching patterns in the figure.

Figure 4:
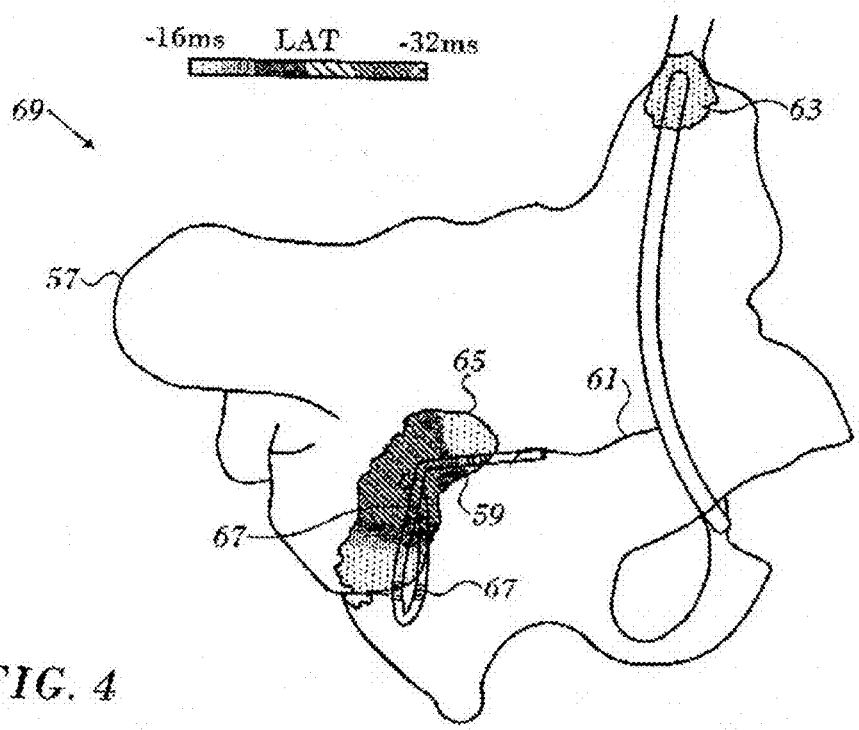
FIG. 4 is screen display at another time during the catheterization shown in FIG. 3 in accordance with an embodiment of the invention.

Reference is now made to FIG. 4, which is another screen display 69 similar to FIG. 3 taken at another time during the catheterization in accordance with an embodiment of the invention. The reconstruction 57 has been rotated in order to better display certain areas of interest. The parameter represented by area 65 has changed, as indicated by differences in coloration compared to FIG. 3.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of catheterization, comprising the steps of:
   inserting a probe into a heart of a living subject, a distal portion of the probe having a plurality of sensors disposed thereon;
   displaying the heart as a first graphic image, the first graphic image displaying nonfunctional electroanatomic information, the first graphic image displayed in a monocolor and iteratively:
   i) processing signals from the sensors to generate respective outputs;
   ii) selecting a region on the first graphic image that is less than all of the first graphic image, the region selected being based on a current location of the plurality of sensors;
   iii) displaying at least a portion of the outputs on the selected region as a second graphic image, the second graphic image displaying functional electroanatomic information, the second graphic image displayed in a pseudocolor; and
   iv) redisplaying a redisplayed first graphic image being in unmodified form by removing the displayed functional electroanatomic information from the selected region of the first graphic image after a predetermined time.

2. The method according to claim 1, wherein the sensors are electrodes and the signals are bioelectric voltages.

3. The method according to claim 2, further comprising determining wavefront propagation and wherein the outputs are local activation times at respective locations of the sensors.

4. The method according to claim 1, wherein the sensors are temperature sensors.

5. The method according to claim 1, wherein the sensors are contact force sensors.

6. The method according to claim 1, wherein the sensors are location sensors.

7. The method according to claim 1, further comprising gating signals from the sensors according to a cardiorespiratory cycle.

8. An apparatus, comprising:
   a probe having a plurality of electrodes and sensors;
   electrical circuitry for receiving data from the electrodes and sensors when the probe is at a location in a heart of a living subject;

one or more processors; and a non-transitory computer readable medium storing a plurality of instructions, which when executed, cause the one or more processors to:

display the heart as a first graphic image, the first graphic image displaying nonfunctional electroanatomic information, the first graphic image displayed in a monocolor and iteratively;

i) process signals from the sensors to generate respective outputs;

ii) select a region on the first graphic image that is less than all of the first graphic image, the region selected being based on a current location of the plurality of sensors;

iii) display at least a portion of the outputs on the selected region as a second graphic image, the second graphic image displaying functional electroanatomic information, the second graphic image displayed in a pseudocolor; and iv) redisplay a redisplayed first graphic image being in unmodified form by removing the displayed functional electroanatomic information from the selected region of the first graphic image after a predetermined time interval.

9. The apparatus according to claim 8, wherein the sensors are electrodes and the signals are bioelectric voltages.

10. The apparatus according to claim 9, wherein the plurality of instructions, when executed, further cause the one or more processors to determine of wavefront propagation and wherein the outputs are local activation times at respective locations of the sensors.

11. The apparatus according to claim 8, wherein the sensors are temperature sensors.

12. The apparatus according to claim 8, wherein the sensors are contact force sensors.

13. The apparatus according to claim 8, wherein the sensors are location sensors.

14. The apparatus according to claim 8, further comprising gating circuitry linked to signals from the sensors, the gating circuitry operative for gating the signals form the sensors according to a cardiorespiratory cycle.

* * * * *